United States Patent [19]

Lee

[11] 4,377,639
[45] Mar. 22, 1983

[54] TISSUE CULTURE DEVICE FOR MASS CELL CULTURE

[75] Inventor: Harold H. Lee, Toledo, Ohio

[73] Assignee: University of Toledo, Toledo, Ohio

[21] Appl. No.: 340,188

[22] Filed: Jan. 18, 1982

[51] Int. Cl.³ .................... C12M 3/04; C12M 3/02; C12M 3/00
[52] U.S. Cl. .................... 435/285; 435/284; 435/286
[58] Field of Search .................... 435/284, 285, 286

[56] References Cited

U.S. PATENT DOCUMENTS

| | | | |
|---|---|---|---|
| 3,028,314 | 4/1962 | Means et al. | 435/75 X |
| 3,062,724 | 11/1962 | Reusser | 435/75 |
| 3,839,155 | 10/1974 | McAleer et al. | 435/285 |
| 3,933,585 | 1/1976 | McAleer et al. | 435/284 X |
| 4,004,981 | 1/1977 | Hurni et al. | 435/312 X |
| 4,065,359 | 12/1977 | Hurni | 435/284 |
| 4,208,483 | 6/1980 | Lee | 435/284 |

Primary Examiner—Robert J. Warden
Attorney, Agent, or Firm—Wilson, Fraser, Barker & Clemens

[57] ABSTRACT

A multiplate, cell propagation device for use in tissue culture having an elongate enclosed vessel containing a plurality of parallel, spaced apart discs secured for rotation within the vessel. The device includes a cradle-like frame for holding the discs in place during rotation thereof, with the entire frame or individual discs being removable from the vessel without disturbing other discs. Means are provided on the frame for selectively holding the discs in place.

7 Claims, 5 Drawing Figures

TISSUE CULTURE DEVICE FOR MASS CELL CULTURE

BACKGROUND OF THE INVENTION

Field of the Invention

This invention relates to tissue culture devices for mass cultivation of cells and in particular to a housing containing a culture disc holder consisting of a cradle-like frame wherein said frame is notched for the positioning, alignment and separation of the culture discs which can be selectively and individually removed or added without removing other discs.

Tissue culture devices having a plurality of spaced apart discs or plates supported on a central rod extending through the disc stack are used in mass cell culture and are shown, for example, in U.S. Pat. Nos. 3,839,155, 4,004,981 and 4,065,359. These devices disclose means for loading the discs upon the shaft which is enclosed within a cylindrical vessel and is provided with means to rotate the discs relative to the vessel through which gases and culture media are passed. Such systems are also shown in commonly-owned U.S. Pat. No. 4,208,483. Similar systems using blades rather than discs are shown in U.S. Pat. Nos. 3,028,314 and 3,062,724. In each of the above patented apparatuses, the discs or blades are supported upon a central axial shaft which requires that the entire shaft be removed from the vessel and then all discs be slipped off the shaft to give access to a given central disc, etc.

SUMMARY OF THE INVENTION

This invention concerns a tissue culture device for cultivation of eucaryotic cells wherein said device utilizes a cradle-like frame which is notched for the alignment and separation of culture discs which can be individually removed or added without removing other discs.

The culture device consists of a cylindrical vessel containing ports for the entrance of substances, including culture medium and nutrient and for the removal of waste substances and other products.

Mounted within the cylindrical bottle is a rotatable culture disc-holder consisting of a cradle-like frame. The frame consists of bars or rods running the length of the vessel wherein said bars contain a plurality of notches, into which fit the culture discs. These discs provide the required substratum and impel the culture medium as the disc-holder is rotated. Cellular attachment can occur on either side of the disc, thereby providing a vast surface area for attachment within a small space.

The cradle-like frame includes at least two notched support surfaces for the discs and a third member extending over the discs to keep them in contact with the notched support surfaces regardless of orientation of the cradle or vessel itself. The third member may be an extensible or elastic band or a movable notched rod which may be pivoted into and out of holding position, as set forth below.

Supports for the rods are provided at both ends whereby said support terminate centrally in an protruding stub which is inserted into a hole in the cylinder at one end to stabilize rotation and is connected to the rotating shaft and motor at the other end.

Other objects and advantages of the invention will be apparent from the following detailed description of a preferred embodiment, with reference made to the accompanying drawings.

DESCRIPTION OF THE PREFERRED EMBODIMENTS

Figure 1:
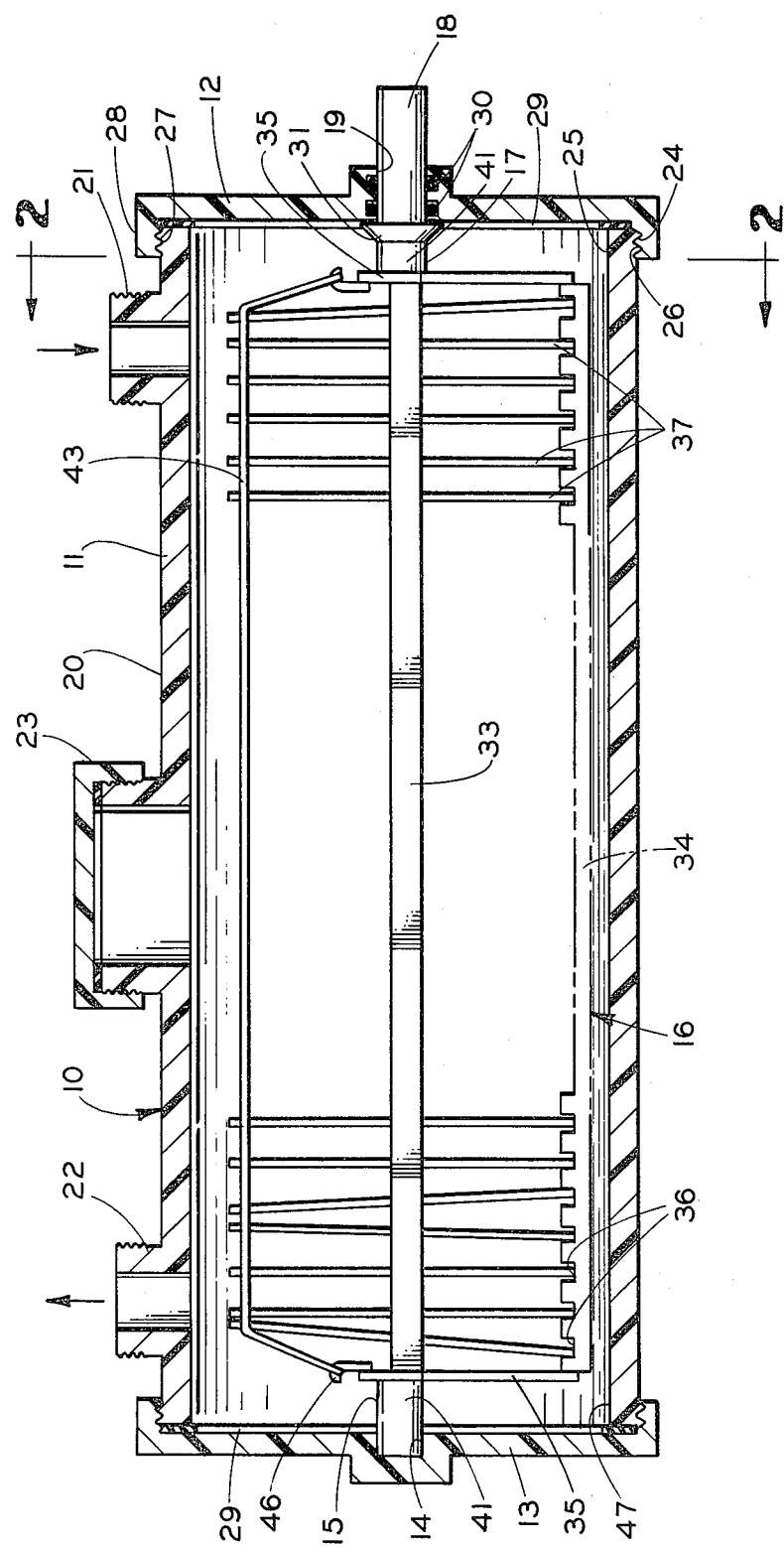
FIG. 1 is an elevational view of the device of this invention; showing the outer vessel in cross-section and a plurality of discs held by the cradle therein.

Referring to FIG. 1 there is shown an elevational view of the tissue culture apparatus 10 according to the present invention. The apparatus 10 consists of an open-ended cylindrical body 11 and a cap 12 threaded over one end and a removable cap 13 on the other end. A central recess 14 in the inner face of the cap 13 supports one end 15 of the culture disc holder 16. The other end 17 of the culture disc holder 16 is attached to the drive shaft 18 extending through an opening 19 in the cap 12 and attaching to a motor, not shown.

The cylindrical exterior 20 of the body 11 has an inlet 21 and an outlet 22 at opposite ends thereof for delivery and discharge of fresh and waste medium respectively, and a centrally positioned auxillary port 23 for entrance and exit of gas. The exterior 20 of the body 11 also includes threads 24 adjacent its open end 25 for engagement with complementary threads 26 around the interior 27 of a downwardly extending cylindrical lip 28 on the cap 12.

A ring seal 29, preferably made of soft silicone rubber, extends about the interior periphery of the cap 12 to provide a fluid tight seal between the cap 12 and the body 11 of the apparatus 10. O-rings 30 seated within the opening 19 of the cap 12 seal against leakage therethrough, and a collar 31 secures the culture disc holder 16 from movement in the axial direction. Similar seals provided on the other cap 13.

Figure 3:
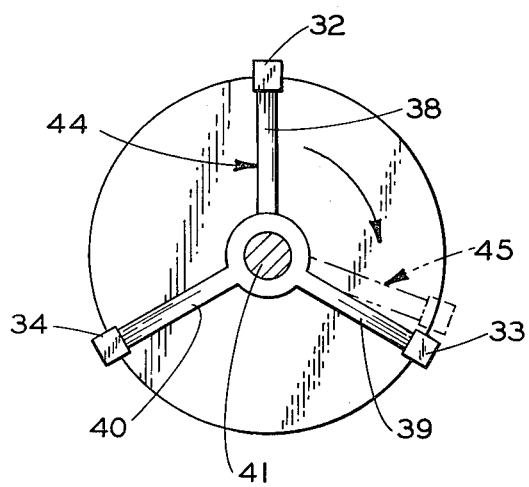
FIG. 3 is an end view showing another embodiment of the cradle support.

The culture disc holder 16 consists of rods 32, 33 and 34 which run the length of the body 11 of the apparatus 10 to form a cradle-like frame, which is also shown in FIG. 3 of cylinder 11. The rods 32, 33 and 34 contain a plurality of notches 36 into which fit individual culture discs 37. Rods 32, 33 and 34 are stabilized by a generally triangular support 35 at both ends 15 and 17 of the disc holder 16.

The supports 35 extend transversely from the notched rods 32, 33 and 34, and support a central stub or support shaft 41 which is seated within the recess 14 at one end 47 of the cylinder 11 to provide a bearing for rotation.

A similar arrangement of supports exits at the other end 25 of the cylinder 11 with the shaft 41 attached to the drive shaft 18 extending through an opening 19 in the cap 12. The drive shaft 18 is a drum shaft for attachment to a suitable drive means, not shown.

Figure 2:
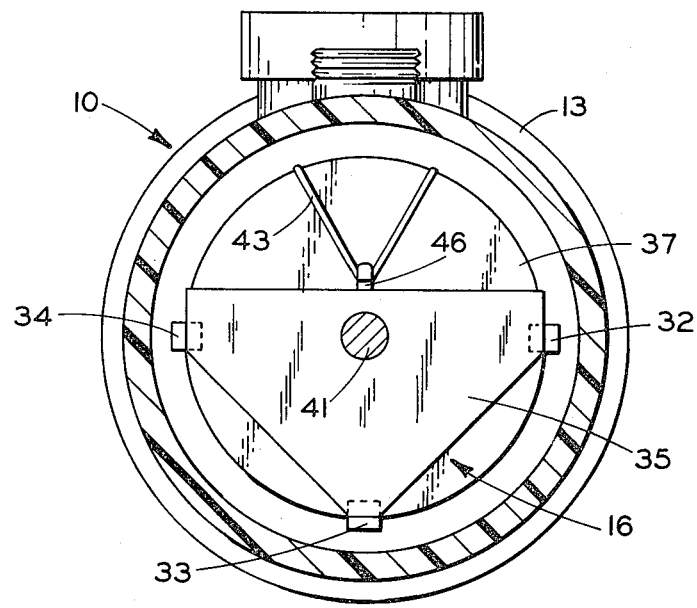
FIG. 2 is an end view in cross-section taken along line 2—2 of FIG. 1 and showing details of one embodiment of the cradle support.

In the embodiment shown in FIGS. 1 and 2, the culture discs 37 are further secured in the holder 16 during rotation by a removable elastic or similar means 43 extending the length of the holder 16, and secured at both ends 15 and 17 of holder 16 on an upwardly extending hook 46.

The culture disc holder is designed for the alignment and separation of culture discs and for selective and individual removal or addition without removal of other discs. Thus, when disc removal or renewal is to be done, the threaded cap 12 is removed and the entire cradle 16 and its discs 37 are axially removed. The elastic means, which is preferably silicone rubber, is removed so that any particular disc 37 is accessible for removal without disturbing the others.

Figure 4:
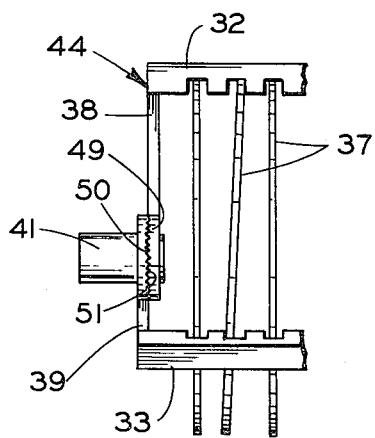
FIG. 4 is an elevational view of the embodiment of FIG. 3 showing certain details of that embodiment.

FIGS. 3 and 4 illustrate an alternate embodiment of the cradle 16 in which an adjustable arm is used in place of the elastic means 43.

FIG. 3 is an end view of the holder 16 showing stationary rods 33 and 34 affixed to support means 39 and 40. Also shown is a movable rod 32 and attached support 38 which together comprise an adjustable arm 44 used in place of the elastic means 43. The adjustable arm 44 is shown in an operating position which stabilizes the disc 37 in the holder 16. To permit loading and removal of the discs 37 when the device 10 is not in operation, the adjustable arm 44 is placed in a non-operational position 45 by pushing inwardly and swinging the arm 44 downwardly to the dotted line postion as indicated of reference number 45.

FIG. 4 is an elevational view of an alternate embodiment of FIG. 3 showing in detail the means by which rotation of the adjustable arm 44 is achieved. The support 38 extending radially from the rod 32 terminates with a ring bearing 49 having a toothed or serrated axially outer face 50 which ring fits over a stub shaft 41 secured rigidly to the fixed support means 39 and 40. Circumjacent the stub shaft 50 is a bearing surface having its inner face with a complimentary toothed or serrated surface 51 which engages the face 50 when the ring bearing 49 is in place on the stub shaft 41. By pushing the adjustable arm 44 inwardly, disengagement of the meshed teeth 50 and 51 occurs, thereby freeing the arm 44, for rotation downward into the non-operational position 45. The arm 44 is secured in the non-operational position 45 by engaging, once again, the toothed surfaces 50 and 51.

Return of the arm 44 from the non-operational position 45 to the upright operation position is achieved similarly, by rotating the arm 44 upwardly.

The other end 17 of the holder 16 duplicates the above described end's 15 structures and mechanism for a rotatable adjustable arm.

Figure 5:
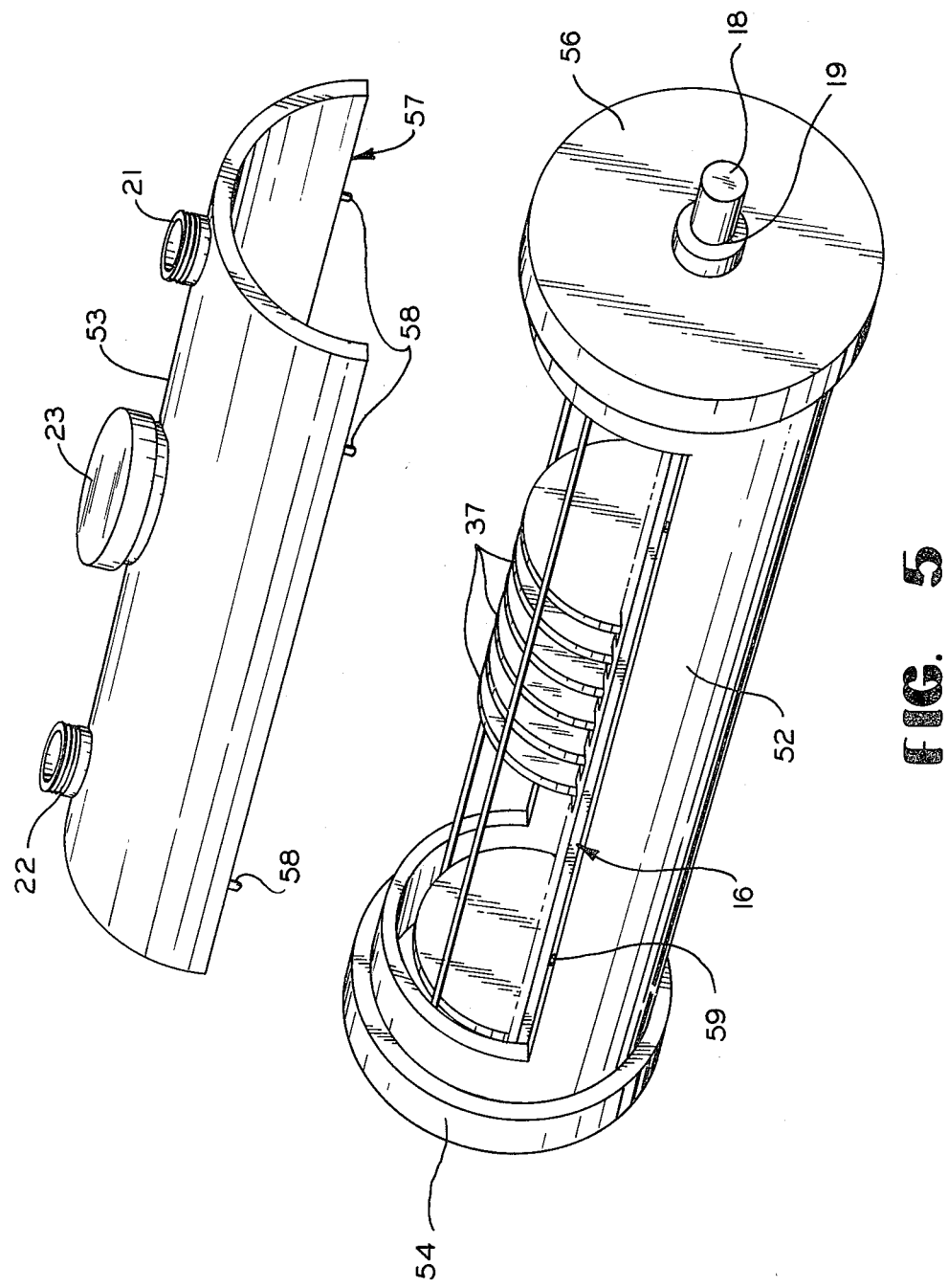
FIG. 5 is an exploded perspective view showing another embodiment of the device of this invention.

FIG. 5 is a perspective view of an alternate embodiment of the tissue culture apparatus 10 shown in FIG. 1. This embodiment consists of an open-topped cylindrical body 52 and a removable lid 53 extending substantially the length of the body. A central recess, not shown, in the inner face of one end 54 of the cylinder 52 supports one end of the culture disc holder 16. The other end of the culture disc holder, not shown, is attached to the drive shaft 18 extending through an opening 19 in the other end 56 of the cylinder 52. The drive shaft 18 is attached to a motor, not shown, as understood from the description of the prior embodiment.

The lid 53 has an inlet 21 and an outlet 22 at opposite ends thereof for delivery and discharge of fresh and waste medium, respectively, and a centrally positioned auxillary port 23 for entrance and exit of gas. The bottom of lid 57 possesses a plurality of downwardly projecting guide pins 58 which are received by corresponding recesses 59 in the cylinder body 52 when the lid 53 is in a closed position. Other equivalent locating and attachment means will be apparent to those skilled in the art.

The culture disc holder 16 is of the same cradle-like frame design described in FIG. 1 or the alternate embodiment described in FIGS. 3 and 4. When disc removal or renewal is necessary, the lid 53 of the cylinder 52 is removed and the entire cradle 16 and its discs 37 are vertically removed. In the event that the entire cradle 16 and its discs 37 are to be removed, the stub shaft 41 is urged out of the recess 14 and the entire cradle 16 is lifted out of the vessel. The construction of the cradle of FIGS. 3 and 4 is particularly advantageous in this embodiment inasmuch as the radial arms 39, 40 and 44 will act as resilient springs to hold the stub shaft 41 in the recess 14 during normal operation but may be temporarily distorted manually towards the center of the cradle to permit removal of the shaft 41 from the recess 14. This embodiment of the culture disc holder also permits the alignment and separation of culture discs and selective and individual removal or addition without removal of other discs. Any particular discs 37 is accessible for removal without disturbing the others, thus making disc changes simple and facile without the necessity of removing the entire cradle itself or other discs.

In accordance with the provisions of the patent statutes, the invention herewith shown and described represents the preferred embodiment and various changes in the shape, size and arrangement of the parts may be resorted to without departing from the spirit of the invention.

What is claimed is:

1. A multiplate, cell propagation device for use in tissue cultures having a generally elongate enclosed vessel with two end caps and containing a plurality of spaced apart circular discs therein with means for rotating said discs within said vessel, the improvement comprising a cradle-like frame adapted for insertion within said enclosed vessel, said frame having spaced apart end plates secured opposite each other by axially extending rods spaced about the lower and lateral periphery of said end plates, a support shaft on the outer face of one of said end plates for engagement with a shaft bearing recess in the adjacent face of the cap on one end of said vessel and a drive shaft on the outer face of a sealed bearing aperture in the adjacent face of the cap on the other end of said vessel, said axially extending rods between said end plates of said frame being positioned at the lowermost and side portions of the periphery of said end plates to support said plurality of spaced apart discs therein and to permit removal thereof via the uppermost portions thereof.

2. The device of claim 1 wherein said axially extending rods include a plurality of radial notches to provide means for holding such discs in spaced apart position within said cradle-like frame.

3. The device of either claims 1 or 2 wherein at least one of said end caps of said enclosed vessel is removable to facilitate removal of said cradle-like frame from said vessel.

4. The device of either claim 1 or 2 wherein said elongate enclosed vessel includes a removable lid in its upper periphery between said end caps, said removable lid extending substantially over the length of said vessel whereby said cradle-like frame and its associated discs may be removed from said vessel through the opening covered by said lid.

5. The device of claim 1 which further includes at least one axially extending rod extending the length of said cradle-like frame and movable from a first position overlying said discs at the uppermost periphery of said end plates to a second position along the side portion of said end plates.

6. The device of claim 1 which further includes an elongate extensible member removably secured to the uppermost portion of each end plate and extending under tension across the uppermost portion of said discs to thereby retain them within said cradle.

7. The device of claim 1 wherein said cradle-like frame includes a pair of spaced apart end plates, each having a central portion for supporting said support shaft and said drive shaft, respectively, and at least two radially extending fixed arms extending from said central portion downwardly and outwardly, an axially extending rod secured to the distal end of each fixed arm and extending between said end plates below said discs to provide support therefore, and a movable arm pivotally secured to said central portion and movable from an upper vertical position to a lateral horizontal position whereby, a movable axially extending rod secured to the distal ends of such movable arms may be selectively positioned above said discs to hold them within said cradle or laterally alongside said discs to permit removal thereof from said cradle.

* * * * *